US00PP36598P2

(12) United States Plant Patent
Trees et al.

(10) Patent No.: US PP36,598 P2
(45) Date of Patent: Apr. 15, 2025

(54) ***BUDDLEIA* PLANT NAMED 'Balchryeel'**

(50) Latin Name: ***Buddleia davidii* X *Buddleia hybrida***
Varietal Denomination: Balchryeel

(71) Applicant: Ball Horticultural Company, West Chicago, IL (US)

(72) Inventors: Scott C. Trees, Arroyo Grande, CA (US); Sarah Kimberly Greenwood, West Chester, PA (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 18/914,980

(22) Filed: Oct. 14, 2024

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./226, 242
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Buddleia* plant named 'Balchryeel', characterized by its compact, upright and outwardly spreading plant habit; moderately vigorous growth habit; freely branching habit; dense and bushy appearance; dark green-colored leaves; and relatively long conical inflorescences with numerous bright violet-colored flowers.

2 Drawing Sheets

Figure 1:
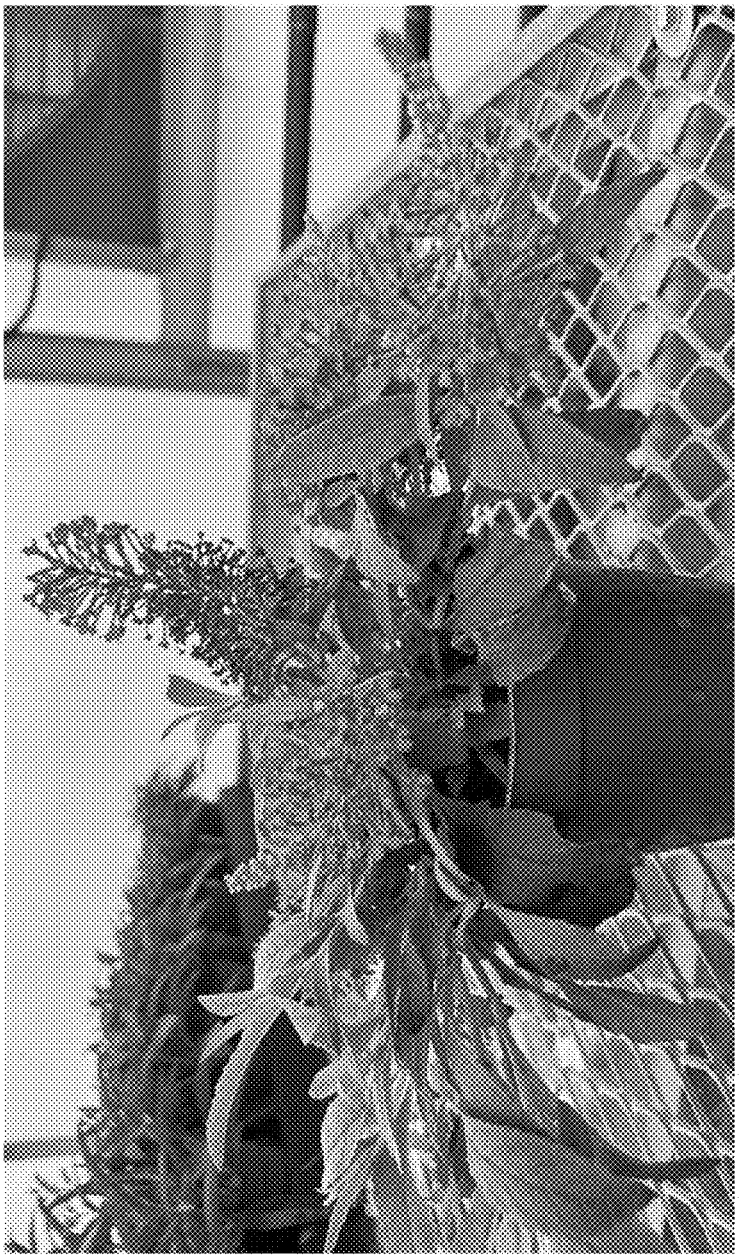

Botanical designation: *Buddleia davidii* X *Buddleia hybrida.*

Cultivar denomination: 'BALCHRYEEL'.

BACKGROUND OF THE INVENTION

The present invention relates to a new and distinct *Buddleia* plant, commonly referred to as Butterfly Bush, botanically known as *Buddleia davidii* X *Buddleia hybrida* and hereinafter referred to by the name 'Balchryeel'.

The new *Buddleia* plant is a product of a planned breeding program conducted by the Inventors in Guadalupe, California and West Grove, Pennsylvania. The objective of the breeding program was to create new *Buddleia* plants with a compact, mounding and freely branching growth habit with numerous flowers and remontant flowering habit.

The new *Buddleia* plant originated from a cross-pollination in Guadalupe, California of *Buddleia davidii* 'Lavender Cascade', disclosed in U.S. Plant Pat. No. 30,635, as the female, or seed, parent with a proprietary selection of *Buddleia hybrida* identified as code number 4548-A, not patented, as the male, or pollen, parent. The new *Buddleia* plant was discovered and selected by the Inventors as a single plant within the progeny of the stated open-pollination in a controlled environment in West Grove, Pennsylvania in August 2020.

Asexual reproduction of the new *Buddleia* plant by terminal stem cuttings in a controlled environments in Guadalupe, California and West Grove, Pennsylvania since August 2020 has shown that the unique features of this new *Buddleia* plant are stable and reproduced true to type in successive generations.

SUMMARY OF THE INVENTION

Plants of the new *Buddleia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Balchryeel'. These characteristics in combination distinguish 'Balchryeel' as a new and distinct *Buddleia* plant:

1. Compact, upright and outwardly spreading plant habit.
2. Moderately vigorous growth habit.
3. Freely branching habit; dense and bushy appearance.
4. Dark green-colored leaves.
5. Relatively long conical inflorescences with numerous bright violet-colored flowers.

Plants of the new *Buddleia* differ primarily from plants of the female parent, 'Lavender Cascade' in flower color as plants of the new *Buddleia* have bright violet-colored flowers whereas plants of 'Lavender Cascade' have light purple-colored flowers. In addition, the lower surfaces of leaves of plants of the new *Buddleia* are medium green in color whereas the lower surfaces of leaves of plants of 'Lavender Cascade' are silvery in color.

Plants of the new *Buddleia* differ primarily from plants of the male parent selection in flower color as plants of the new *Buddleia* have bright violet-colored flowers whereas plants of the male parent selection have dark purple-colored flowers. In addition, the lower surfaces of leaves of plants of the new *Buddleia* are medium green in color whereas the lower surfaces of leaves of plants of 'Lavender Cascade' are silvery in color.

Plants of the new *Buddleia* can be compared to plants of *Buddleia davidii* 'Tobudpipur', disclosed in U.S. Plant Pat. No. 22,064. In side-by-side comparisons, plants of the new *Buddleia* differ primarily from plants of 'Tobudpipur' in flower color as plants of the new *Buddleia* have bright violet-colored flowers whereas plants of 'Tobudpipur' have dark purple-colored flowers. In addition, plants of the new

*Buddleia* are more outwardly spreading than and not as upright as plants of 'Tobudpipur'.

BRIEF DESCRIPTION OF THE PHOTOGRAPHS

The accompanying colored photographs illustrate the overall appearance of the new *Buddleia* plant showing the colors as true as it is reasonably possible to obtain in colored reproductions of this type. Colors in the photographs may differ slightly from the color values cited in the detailed botanical description which accurately describe the colors of the new *Buddleia* plant.

The photograph on the first sheet (FIG. 1) is a side perspective view of a typical flowering plant of 'Balchryeel' grown in a container.

Figure 2:
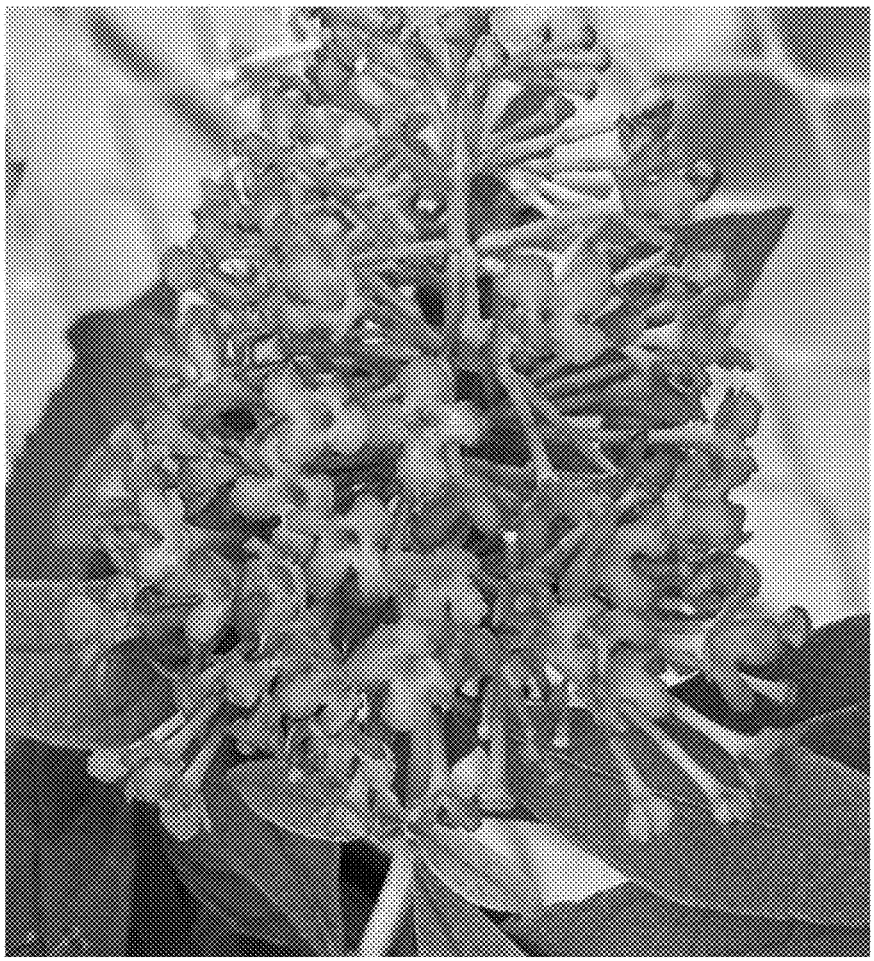

The photograph on the second sheet (FIG. 2) is a close-up view of a typical inflorescence of 'Balchryeel'.

DETAILED BOTANICAL DESCRIPTION

The aforementioned photographs and following observations and measurements describe plants grown in 10-cm containers in a polyethylene-covered greenhouse in West Chicago, Illinois during the late winter and early spring and under cultural practices similar to those used in commercial *Buddleias* plant production. During the production of the plants, day temperatures averaged 25° C. and night temperatures averaged 10° C. Plants were pinched twice and were twelve weeks from planting rooted young plants when the photographs and description were taken. In the following description, color references are made to The Royal Horticultural Society Colour Chart, Sixth Edition, except where general terms of ordinary dictionary significance are used. Measurements represent averages for typical flowering plants.

Botanical classification: *Buddleia davidii* X *Buddleia hybrida* 'Balchryeel'.

Parentage:

*Female, or seed, parent.*—*Buddleia davidii* 'Lavender Cascade', disclosed in U.S. Plant Pat. No. 30,635.

*Male, or pollen, parent.*—Proprietary selection of *Buddleia hybrida* identified as code number 4548-A, not patented.

Propagation:

*Type.*—By terminal stem cuttings.

*Time to initiate roots plant.*—About two to three weeks.

*Time to produce a rooted plant.*—About six to seven weeks.

*Root description.*—Fine, fibrous; typical creamy white in color, however actual color of the roots is dependent on substrate composition, water quality, fertilizer, substrate temperature and physiological age of roots.

*Rooting habit.*—Freely branching; medium density.

Plant description:

*Plant and growth habit.*—Deciduous perennial; compact, upright and outwardly spreading plant habit; freely branching habit, dense and bushy appearance; moderately vigorous growth habit and moderate growth rate.

*Plant height.*—About 10 cm to 13 cm.

*Plant width (spread).*—About 26 cm to 30 cm.

*Lateral branches.*—Quantity: Freely branching habit with about seven to eight primary lateral branches developing per plant with secondary lateral branches potentially developing at every node. Length: About 10 cm to 13 cm. Diameter: About 2 mm to 2.5 mm. Internode length: Relatively short, about 1.5 cm. Strength: Strong, flexible. Aspect: Initially upright to about 60° from vertical; with subsequent development, close to horizontal. Texture and luster: Initially, soft pubescent, then becoming glabrous and woody with development; matte. Color, developing: Close to 144A; pubescence, close to 193A. Color, woody: Close to 199A.

Leaf description:

*Arrangement and appearance.*—Opposite, simple.

*Length.*—About 6 cm to 6.5 cm.

*Width.*—About 1.8 cm to 2.2 cm.

*Shape.*—Narrowly elliptic.

*Apex.*—Narrowly acute.

*Base.*—Cuneate to attenuate.

*Margin.*—Serrate; slightly undulate.

*Texture and luster, upper and lower surfaces.*—Smooth, glabrous; matte to slightly glossy.

*Venation pattern.*—Pinnate.

*Color.*—Developing and fully expanded leaves, upper surface: Close to 147A; venation, close to 146A Developing and fully expanded leaves, lower surface: Close to 147C; venation, close to 146B to 146C.

*Petioles.*—Length: About 6 mm to 7 mm. Diameter: About 1 mm to 1.25 mm. Texture and luster, upper and lower surfaces: Smooth, glabrous; matte to slightly glossy. Strength: Moderately strong, flexible. Color, upper surface: Close to 144A. Color, lower surface: Close to between 144A and 146A.

Flower description:

*Flower type and flowering habit.*—Single salverform flowers arranged on terminal panicles; inflorescences face upright to mostly outwardly; panicles long and conical in shape; freely flowering habit with about 225 to 275 flowers developing per inflorescence and about 12 to 15 inflorescences in various stages of development at one time; flowers face upright, outwardly to downward depending on position on the panicle; flowers persistent.

*Fragrance.*—Faintly fragrant; sweet and pleasant.

*Natural flowering season.*—Long flowering period, plants flower continuously from throughout the summer in north central Texas.

*Inflorescence buds.*—Height: About 6 mm. Diameter: About 2 mm. Shape: Narrowly ovoid. Color: Close to 144A.

*Flower buds.*—Height: About 2 mm to 3 mm. Diameter: About 1 mm to 2 mm. Shape: Narrowly ovoid. Color: Close to 144A.

*Inflorescence length.*—About 10 cm to 10.5 cm.

*Inflorescence diameter.*—About 2.75 cm to 3 cm.

*Flower diameter.*—About 6 mm.

*Flower depth (height).*—About 1.3 cm.

*Throat diameter.*—About 1.5 mm to 2 mm.

*Tube length.*—About 1 cm.

*Tube diameter, proximally.*—About 1.5 mm to 2 mm.

*Petals.*—Quantity per flower: Typically four in a single whorl fused at the base. Lobe length: About 2 mm to 2.5 mm. Lobe width: About 2 mm to 2.25 mm. Lobe shape: Spatulate. Lobe apex: Obtuse. Lobe margin: Entire; slightly undulate. Lobe texture and luster, upper and lower surfaces: Smooth, glabrous; matte. Lobe color: Developing and fully expanded petals, upper surface: Close to 94C; venation, close to 94C; color becoming closer to 94D with development. Developing and fully expanded petals, lower surface: Close to 94D; venation, close to 94D; color does not change with subsequent development. Throat: Close to 28A. Tube: Close to 94D.

*Sepals*.—Quantity per flower: Typically four in a single whorl. Length: About 2 mm to 3 mm. Width: Less than 1 mm. Shape: Narrowly ovate to lanceolate. Apex: Acute. Base: Fused at the base. Margin: Entire. Texture, upper and lower surfaces: Smooth, glabrous. Color, upper and lower surfaces: Close to 144A.

*Peduncles*.—Length: About 7 mm to 9 mm. Diameter: About 1 mm. Strength: Strong, wiry. Angle: About 45° to 90° from vertical. Texture: Slightly pubescent. Color: Close to between 144A and 146A.

*Pedicels*.—Length: About 2 mm to 3 mm. Diameter: Less than 1 mm. Strength: Strong, wiry. Angle: Outwardly. Texture: Slightly pubescent. Color: Close to 144A to 144B.

*Reproductive organs*.—Stamens: Quantity per flower: Typically four. Filament length: About 0.5 mm. Filament color: Close to 27D. Anther length: About 1 mm. Anther shape: Oblong. Anther color: Close to 157C. Pollen amount: None observed. Pistils: Quantity per flower: One. Pistil length: About 1 mm. Stigma shape: Oblong. Stigma color: Close to 144A to 144B.

*Seeds and fruits*.—To date, seed and fruit development have not been observed on plants of the new *Buddleia*.

Pathogen & pest resistance: To date, plants of the new *Buddleia* have not been observed to be resistant to pathogens and pests common to *Buddleia* plants.

It is claimed:

1. A new and distinct *Buddleia* plant named 'Balchryeel' as herein illustrated and described.

* * * * *